US008642091B2

(12) United States Patent
Shekunov et al.

(10) Patent No.: US 8,642,091 B2
(45) Date of Patent: *Feb. 4, 2014

(54) METHOD FOR PRODUCING SOLID-LIPID COMPOSITE DRUG PARTICLES

(75) Inventors: Boris Y. Shekunov, Aurora, OH (US); Pratibhash Chattopadhyay, North Royalton, OH (US); Robert W. Huff, North Royalton, OH (US)

(73) Assignee: Ferro Corporation, Cleveland, OH (US)

( * ) Notice: Subject to any disclaimer, the term of this patent is extended or adjusted under 35 U.S.C. 154(b) by 989 days.

This patent is subject to a terminal disclaimer.

(21) Appl. No.: 12/124,518

(22) Filed: May 21, 2008

(65) Prior Publication Data

US 2008/0286365 A1 Nov. 20, 2008

Related U.S. Application Data

(63) Continuation of application No. 11/160,367, filed on Jun. 21, 2005, now abandoned, which is a continuation-in-part of application No. 10/434,426, filed on May 8, 2003, now Pat. No. 7,083,748.

(51) Int. Cl.
*B29B 9/00* (2006.01)
*A61K 9/14* (2006.01)
*A61K 9/00* (2006.01)
*A61K 9/16* (2006.01)

(52) U.S. Cl.
USPC ............... 424/489; 424/400; 424/498; 264/5

(58) Field of Classification Search
None
See application file for complete search history.

(56) References Cited

U.S. PATENT DOCUMENTS

| | | | |
|---|---|---|---|
| 4,177,177 A | 12/1979 | Vanderhoff et al. | |
| 4,582,731 A | 4/1986 | Smith | |
| 4,687,661 A | * 8/1987 | Kikuchi et al. | 124/38 |
| 4,734,451 A | 3/1988 | Smith | |
| 4,744,926 A | 5/1988 | Rice | |
| 4,898,673 A | 2/1990 | Rice et al. | |
| 5,011,819 A | 4/1991 | Leibovitz | |
| 5,043,280 A | 8/1991 | Fischer et al. | |
| 5,158,704 A | 10/1992 | Fulton et al. | |
| 5,189,107 A | 2/1993 | Kasai et al. | |
| 5,216,065 A | 6/1993 | Colyer et al. | |
| 5,244,768 A | 9/1993 | Inaba | |
| 5,266,205 A | 11/1993 | Fulton et al. | |
| 5,360,478 A | 11/1994 | Krukonis et al. | |
| 5,389,263 A | 2/1995 | Gallagher et al. | |
| 5,399,597 A | 3/1995 | Mandel et al. | |
| 5,440,055 A | 8/1995 | Castor | |
| 5,494,683 A | 2/1996 | Liversidge et al. | |
| 5,548,004 A | 8/1996 | Mandel et al. | |
| 5,554,382 A | 9/1996 | Castor | |
| 5,578,650 A | 11/1996 | Delgado et al. | |
| 5,622,649 A | 4/1997 | Hunter et al. | |
| 5,639,441 A | 6/1997 | Sievers et al. | |
| 5,674,911 A | 10/1997 | Emanuele et al. | |
| 5,691,387 A | 11/1997 | Emanuele et al. | |
| 5,696,298 A | 12/1997 | Emanuele et al. | |
| 5,707,634 A | 1/1998 | Schmitt | |
| 5,707,673 A | 1/1998 | Prevost et al. | |
| 5,727,333 A | 3/1998 | Folan | |
| 5,750,679 A | 5/1998 | Haas et al. | |
| 5,750,709 A | 5/1998 | Castor | |
| 5,766,636 A | 6/1998 | Turk et al. | |
| 5,766,637 A | 6/1998 | Shine et al. | |
| 5,770,559 A | 6/1998 | Manning et al. | |
| 5,776,486 A | 7/1998 | Castor et al. | |
| 5,789,505 A | 8/1998 | Wilkinson et al. | |
| 5,827,522 A | 10/1998 | Nowak | |
| 5,863,696 A | 1/1999 | Koyama et al. | |
| 5,874,029 A | 2/1999 | Subramaniam et al. | |
| 5,921,478 A | 7/1999 | Kamiwano et al. | |
| 5,981,474 A | 11/1999 | Manning et al. | |
| 5,990,241 A | 11/1999 | Emanuele et al. | |
| 5,993,747 A | 11/1999 | Mandel | |
| 5,993,850 A | 11/1999 | Sankaram et al. | |
| RE36,665 E | 4/2000 | Emanuele et al. | |
| 6,087,003 A | 7/2000 | Benoit et al. | |
| 6,095,134 A | 8/2000 | Sievers et al. | |

(Continued)

FOREIGN PATENT DOCUMENTS

| | | |
|---|---|---|
| JP | 1-158042 | 6/1989 |
| WO | 95/01221 | 1/1995 |
| WO | 97/14407 A1 | 4/1997 |
| WO | 03/000192 A2 | 1/2003 |

OTHER PUBLICATIONS

Preparing Soap ('Soap'), 5 pages.*
Preparing Soap, 5 pages, 2003.*
Sjostrom et al., "Preparation of submicron drug particles in lecithin-stabilized o/w emulsions: I. Model studies of the precipitation . . . ," International Journal of Pharm., 84 (1992) pp. 107-116.
Sjostrom et al., "Preparation of submicron drug particles in lecithin-stabilized o/w emulsions: I. Model studies of the precipitation . . . ," International Journal of Pharm., 88 (1992) pp. 53-62.
Kawano et al., "Characteristics of Biodegradable Microcapsules by Solvent Evaporation in (W/O/W) Emulsion System," Journal of Chem. Eng. of Japan, vol. 34, No. 9, (2001) pp. 1182-1186.
Nakajima et al., "Recent Studies on Super-Hydrophobic Films," Monatshefte fur Chemie 132, (2001) pp. 31-41.
Chung et al., "Effects of the rate of solvent evaporation on the characteristics of drug loaded PLLA and PDLLA microspheres," International Journal of Pharm., 212 (2001) pp. 161-169.

*Primary Examiner* — Kyle Purdy
(74) *Attorney, Agent, or Firm* — Rankin, Hill & Clark LLP

(57) ABSTRACT

A method of producing solid composite lipid/drug nanoparticles that includes the steps of: (1) dissolving a lipid and a drug in a suitable organic solvent to form a solution; (2) emulsifying the solution in a liquid to form an emulsion having a discontinuous phase of micelles comprising the organic solvent, the drug and the lipid, and a continuous phase comprising the liquid; and (3) contacting the emulsion with a supercritical fluid under conditions suitable to keep the supercritical fluid in a supercritical state, whereby the supercritical fluid extracts the organic solvent from the micelles, causing them to precipitate as organic-solvent free solid composite lipid/drug nanoparticles suspended or dispersed in the liquid.

7 Claims, 7 Drawing Sheets

(56) References Cited

U.S. PATENT DOCUMENTS

| | | |
|---|---|---|
| 6,106,720 A | 8/2000 | Kanel et al. |
| 6,214,384 B1 | 4/2001 | Pallado et al. |
| 6,228,399 B1 | 5/2001 | Parikh et al. |
| 6,235,701 B1 | 5/2001 | Senger Elsbernd |
| 6,248,363 B1 | 6/2001 | Patel et al. |
| RE37,285 E | 7/2001 | Emanuele et al. |
| 6,291,013 B1 | 9/2001 | Gibson et al. |
| 6,299,906 B1 | 10/2001 | Bausch et al. |
| 6,359,014 B1 | 3/2002 | Emanuele et al. |
| 6,372,260 B1 | 4/2002 | Andersson et al. |
| 6,380,302 B1 | 4/2002 | Ikenaga et al. |
| 6,384,090 B2 | 5/2002 | Riede et al. |
| 6,391,452 B1 | 5/2002 | Antonsen et al. |
| 6,414,050 B1 | 7/2002 | Howdle et al. |
| 6,416,742 B1 | 7/2002 | Stefely et al. |
| 6,440,431 B1 | 8/2002 | Yoshida et al. |
| 6,440,493 B1 | 8/2002 | Gibson et al. |
| 6,479,584 B1 | 11/2002 | Nakagawa et al. |
| 6,540,393 B1 | 4/2003 | Lyons et al. |
| 7,083,748 B2 | 8/2006 | Chattopadhyay et al. |
| 2004/0026319 A1* | 2/2004 | Chattopadhyay et al. .... 210/634 |
| 2006/0039983 A1 | 2/2006 | Shekunov et al. |

\* cited by examiner

METHOD FOR PRODUCING SOLID-LIPID COMPOSITE DRUG PARTICLES

CROSS-REFERENCE TO RELATED APPLICATIONS

The present application is a continuation of application Ser. No. 11/160,367 filed Jun. 21, 2005 which is a continuation-in-part of application Ser. No. 10/434,426, filed May 8, 2003, both of which applications are incorporated herein by reference in their entirety.

BACKGROUND OF THE INVENTION

1. Field of Invention

The present invention relates generally to an apparatus and a method of producing solid-lipid composite drug particles.

2. Description of Related Art

In recent years, solid composite lipid/drug particles have been used for oral, pulmonary and parenteral drug delivery as an alternative to traditional drug delivery systems such as emulsions, liposomes and biodegradable polymer nanoparticles. Solid lipid/drug composite particles provide the advantages of traditional drug delivery systems, such as improved dissolution and controlled release, but avoid some of the disadvantages of traditional drug delivery systems. The use of drug-containing emulsions, for example, is limited by the physical stability of the drug-containing emulsions, and also by the low dissolution of most drugs in the triglycerides used to form the emulsions. Liposome based drug delivery systems are limited by the non-availability of inexpensive pharmaceutical liposomes, and also by the low solubility of most drugs in the liposome membrane. Biodegradable polymer nanoparticles are limited by the cytotoxicity of certain polymers in the human body.

Most lipids are well tolerated by the human body and do not cause undesirable side effects upon delivery. Thus, they are particularly suitable for use in delivering drugs. Conventional methods of making solid composite lipid/drug particles include: the high-pressure homogenization process, which is described by Lucks et al. in EP 0 605 497; the microemulsion process, which is described by Gasco in U.S. Pat. No. 5,250,236; the precipitation process, which is described by Siekmann and Westesen in *Preparation And Physicochemical Characterization Of Aqueous Dispersions Of Coenzyme $Q_{10}$ Nanoparticles*, Pharm Res. 1995; 12:201-208; and the nanopelletization process, which is described by Domb in U.S. Pat. No. 5,188,837.

There are some inherent limitations on the conventional methods of forming solid composite lipid/drug particles. The high-pressure homogenization process, for example, is limited by the solubility of the drug in the molten lipid, and cannot be used to effectively produce solid composite lipid/drug particles having an average particle diameter of less than 100 nm. The average particle size of solid composite lipid/drug particles produced via the microemulsion process tends to be quite small, but the dispersion obtained using this process is extremely dilute and is thus not suitable for drug delivery applications. And, although the precipitation process can be used to produce fine particles having average diameters in the nanometer range, large processing times are required in order to achieve low residual solvent content. Scale up of the process is also problematic.

BRIEF SUMMARY OF THE INVENTION

The present invention provides an apparatus and a method of producing solid composite lipid/drug nanoparticles for controlled drug delivery that offers several advantages over conventional processing techniques, including the consistent production of solid composite lipid/drug particles having an average diameter below 100 nm, high drug loading and low temperature processing. The method of the invention is sometimes referred to herein by the acronym PSFEE, which stands for Particles from Supercritical Fluid Extraction of Emulsions ("PSFEE"), and involves the steps of: (1) dissolving a lipid and a drug in a suitable organic solvent to form a solution; (2) emulsifying the solution in a liquid to form an emulsion having a discontinuous phase of micelles comprising the organic solvent, the drug and the lipid, and a continuous phase comprising the liquid; and (3) contacting the emulsion with a supercritical fluid under conditions suitable to keep the supercritical fluid in a supercritical state, whereby the supercritical fluid extracts the organic solvent from the micelles, causing them to precipitate as organic-solvent free solid composite lipid/drug nanoparticles suspended or dispersed in the liquid.

The foregoing and other features of the invention are hereinafter more fully described and particularly pointed out in the claims, the following description setting forth in detail certain illustrative embodiments of the invention, these being indicative, however, of but a few of the various ways in which the principles of the present invention may be employed.

DETAILED DESCRIPTION OF THE INVENTION

Figure 1:
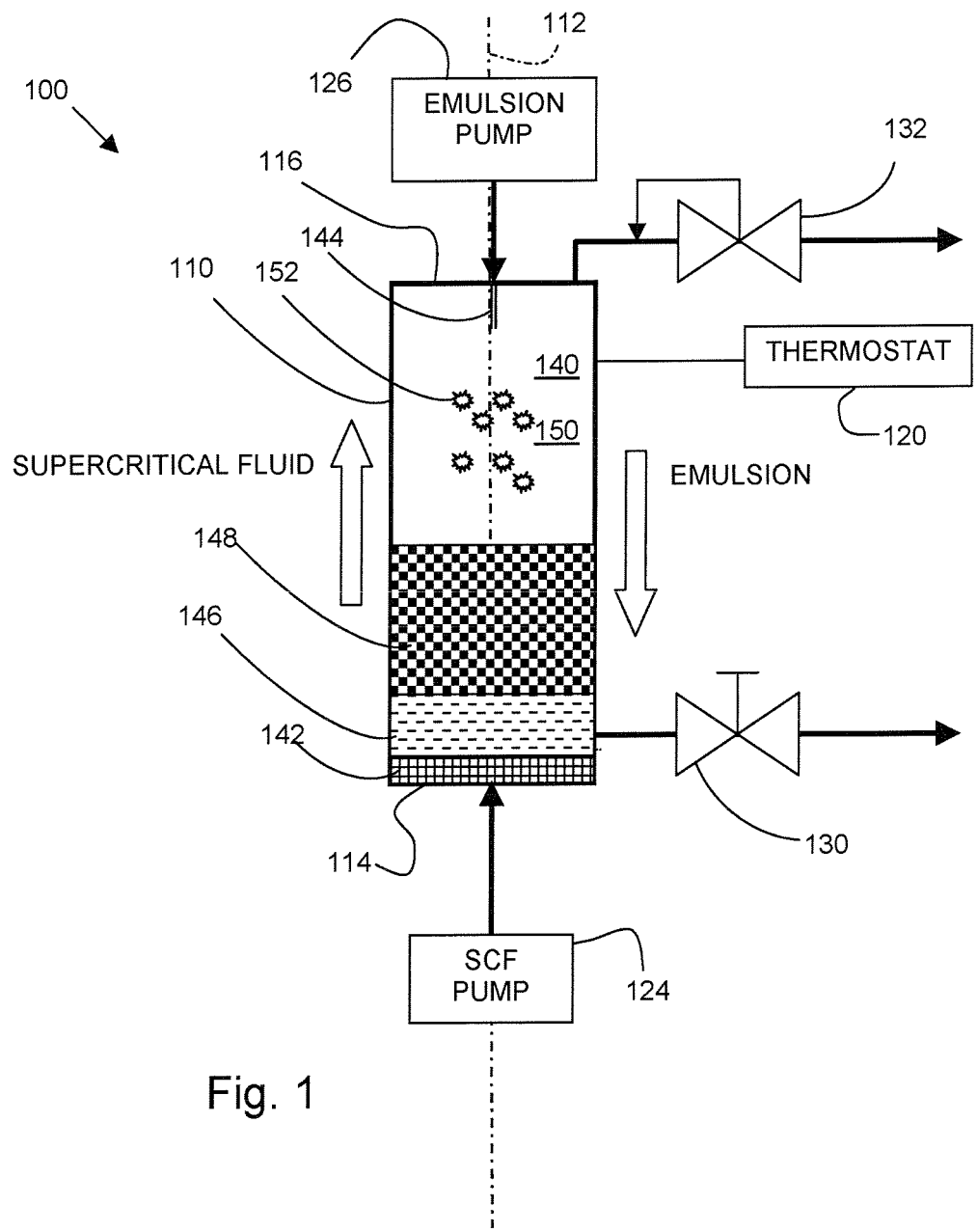
FIG. 1 is a schematic drawing of a first apparatus for use in accordance with a method of the invention.

The present invention provides a method of producing solid composite lipid/drug nanoparticles that are dispersed or suspended in a liquid. Throughout the instant specification and in the appended claims, the term "lipid" refers to fats and fat derived materials (e.g., fatty acids, fatty acid esters, fatty alcohols, sterols, and waxes) that are relatively insoluble in water, are utilizable by animal organisms and are solids phase materials at 1 atmosphere pressure and 15° C. temperature. A preferred lipid for use in the invention is polyethylene gylcol-32 glyceryl palmitostearate, which is available from Gattefosse SA as GELUCIRE 50/13. Another preferred lipid is tripalmitin.

The term "drug" refers to any substance that is intended for use in the diagnosis, cure, mitigation, treatment or prevention of diseases or health conditions and/or to affect the structure or function of the body. Included within the definition are synthetic and natural medicinal agents, pharmaceuticals, dietary supplements and vitamins.

The term "liquid", unless otherwise specifically defined, refers to substances that are liquid phase fluids at 1 atmosphere pressure and 15° C. temperature. Water is the preferred liquid for use in the invention, but other liquids that can emulsify an organic solution comprising a dissolved lipid and drug can also be used.

In accordance with the method of the invention, at least one lipid and at least one drug are dissolved in at least one organic solvent to form a solution. The weight ratio of drug(s) to lipid(s) dissolved in the organic solvent can be from about 0.1:99.9 to about 50:50. More preferably, however, the weight ratio of drug(s) to lipid(s) will be from about 5:95 to about 40:60. The amount of organic solvent in the solution will depend upon the solvating power of the organic solvent with respect to the lipid and drug, and the desired viscosity of the resulting solution. Typical drug/lipid loadings are from about 1% to about 50% by weight of the organic solvent. Suitable organic solvents for use in the invention include, for example, chloroform, toluene, hexane, ethyl acetate and other organic solvents that have good solvating power for lipids and drugs and which can be emulsified in water or other liquids.

The organic solution is emulsified in a liquid to form an emulsion having a discontinuous phase of micelles comprising the organic solvent, the drug and the lipid, and a continuous phase comprising the liquid. Surfactants can, if necessary, be present in the liquid before the emulsifying step. Co-surfactants can, if necessary, be present in the organic solution before the emulsifying step. Surfactants and co-surfactants can help stabilize the emulsion and the resulting particles formed upon processing. The surfactants and co-surfactants are preferably biodegradable and pharmaceutically accepted surfactants. However, emulsion systems can also be formed with very little or no surfactant to achieve short-term emulsion stability required for the duration of a supercritical fluid process according to the invention. Preferred surfactants include non-ionic, anionic and cationic surfactants. Preferred emulsifiers include poly(vinyl pyrrolidone), polyglycerol, polyricinoleate, poly(vinyl alcohol), and block copolymers.

Once the emulsion is formed, it is contacted with a supercritical fluid under conditions suitable to keep the supercritical fluid in a supercritical state. The contacting step is preferably accomplished by injecting the emulsion and the supercritical fluid into a heated pressure vessel. The organic solvent must be soluble in the supercritical fluid, such that the supercritical fluid extracts the organic solvent from the micelles, causing them to precipitate as organic-solvent free solid composite lipid/drug nanoparticles that become suspended or dispersed in the liquid. The supercritical fluid is preferably supercritical carbon dioxide ("$CO_2$"). However, supercritical fluids such as trifluoro methane, ammonia, nitrous oxide, dimethylether, straight chain or branched C1-C6 alkanes, alkenes, alcohols, and combinations thereof could be used. The supercritical fluid is chosen generally with reference to the solubility of at least one of the solvents present in the emulsion. Supercritical $CO_2$ is very effective in removing organic solvents from organic solutions comprising dissolved lipids and drugs.

FIG. 1 is a schematic representation of an apparatus 100 for producing solid composite lipid/drug nanoparticles in accordance with the method of the invention wherein the emulsion and the supercritical fluid are introduced into the pressure vessel using a "contra-current" flow. The apparatus 100 includes a reactor or extractor 110, which is preferably tubular and defines an axis 112 and having first and second ends 14, 116 that are spaced axially apart. Preferably, the axis 112 is oriented vertically such that the first end 114 is below the second end 116. That is, the second end 116 is UP and the first end 114 is DOWN when moving along the axis 112. The extractor 110 is preferably about 1 to about 5 meters long, although other lengths and configurations can be employed.

A thermostat 120 communicates with heating elements (not shown) that are located proximate to the extractor 110. A supercritical fluid pump 124 communicates with the first end 114 of the extractor 110, and an emulsion pump 126 communicates with the second end 116 of the extractor 110. A release valve 130 and a backpressure regulator 132 also communicate with the extractor 110.

The extractor 110 has an inner surface that defines an extraction chamber 140. Preferably disposed within the extraction chamber 140 are optional parts, for example a frit 142, a nozzle 144 and a packed bed 148. If an optional packed bed 148 is employed, the portion of the chamber 140 that is not occupied by the packed bed 148 defines an upper portion or headspace 150.

The supercritical fluid pump 124 is preferably a P-200 high-pressure reciprocating pump commercially available from Thar Technologies, Inc. (Pittsburgh, Pa.). Suitable alternative pumps include diaphragm pumps and air-actuated pumps that provide a continuous flow of supercritical fluid. Preferably, the supercritical fluid pump 124 can be supplemented with a surge tank and metering valve (not shown) so as produce a pulse-free flow. The source of the supercritical fluid can be a virgin source or can be a recycled source. If recycled, the "dirty" or solvent bearing supercritical fluid is expanded to separate the solvent from the supercritical fluid. The supercritical fluid is then compressed and reused as the supercritical fluid supply or source.

The frit 142 is preferably stainless steel and has a pore size of preferably about 0.5 micrometer (μm) or smaller. The frit 142 overlays the inner surface of the extractor 110 at the extractor first end 114. The supercritical fluid pump 124 is in fluid communication with the frit 142 and supplies supercritical fluid through the frit 142 into the extraction chamber 140. The frit 142 is micro-porous and the supercritical fluid flows through the frit 142 and breaks into a plurality of dispersed flow streams.

The solution pump 126 is preferably a high-pressure liquid-chromatography (HPLC) reciprocating pump such as the model PU-2080, which is commercially available from Jasco Inc. (Easton, Md.). Suitable alternative pumps include syringe type pumps, such as the 1000D or 260D pumps, which are commercially available from Isco Inc. (Lincoln, Nebr.).

The nozzle 144 is preferably a capillary-type nozzle and extends from the inner surface of the extractor 110 at the second end 116 into the extraction chamber 140. The emulsion pump 126 is in fluid communication with the nozzle 144 and supplies an emulsion (discussed in further detail hereinbelow) through the nozzle 144 into the extraction chamber 140. A head or end of the nozzle 144 that extends into the extraction chamber 140 may define a plurality of openings having very small diameters of uniform size. The diameter of the openings can affect the droplet size. Thus, controlling the opening diameters can control the size of the resultant emulsion droplets. Alternatively, a nozzle is provided such that, rather than spraying, the emulsion is pumped through the chamber 140. It is preferably that a pumped emulsion has an increased retention time and/or an increased volume of packed bed so as to effect a sufficient contact time and surface area between the flows of supercritical fluid and emulsion.

The packed bed 148 is preferred but optional. Use of a packed bed 148 can increase the extraction efficiency of an extraction column. If present, the packed bed 148 occupies a substantial volume of the extraction chamber 140. The packed bed 148 is preferably Raschig rings, which are commercially available from Labglass, Inc. an SP Industries Company (Vineland, N.J.). In alternative embodiments, the packed bed is comprised of glass beads, ceramic pellets, glass wool, zeolite, catalyst, stainless steel wool, and/or the like. Alternatively, the packed bed 148 is a series of trays that extend a flow path length through the expansion chamber 140. The remaining, upper portion 150 of the extraction chamber 140 is generally unobstructed so that the emulsion and the supercritical fluid can flow therethrough. The headspace or upper portion 150 is preferably occupied or pre-charged with supercritical fluid.

Upon contacting the supercritical fluid, the organic solvent is extracted from the discontinuous phase of the emulsion (i.e., the micelles) causing the lipid and drug to precipitate into the liquid as a dispersion or suspension of solid composite lipid/drug nanoparticles 146, which is preferably separate from the supercritical fluid bearing the organic solvent. The liquid suspension or dispersion of solid composite lipid/drug nanoparticles collects adjacent to the frit 142 at the first end 114, or bottom, of the chamber 140. A release valve 130 is in fluid communication with this portion of the chamber, and allows for the removal of the liquid dispersion or suspension of solid composite lipid/drug nanoparticles 146. The release valve 130 is preferably a standard commercially available valve and is interchangeable with other like valves that are known to those of ordinary skill in the art.

A backpressure regulator 132 is preferably a 26-1700 type regulator, which is commercially available from Tescom, USA (Elk River, Minn.). is used to remove supercritical fluid bearing the organic solvent.

During a contra-current operation of the apparatus 100, the extractor 110 is maintained at constant operating temperature by the thermostat 120. The extraction chamber 140 is brought up to a predetermined pressure, preferably using the supercritical fluid pump 124. The upper portion 150 fills with supercritical fluid.

Figure 4:
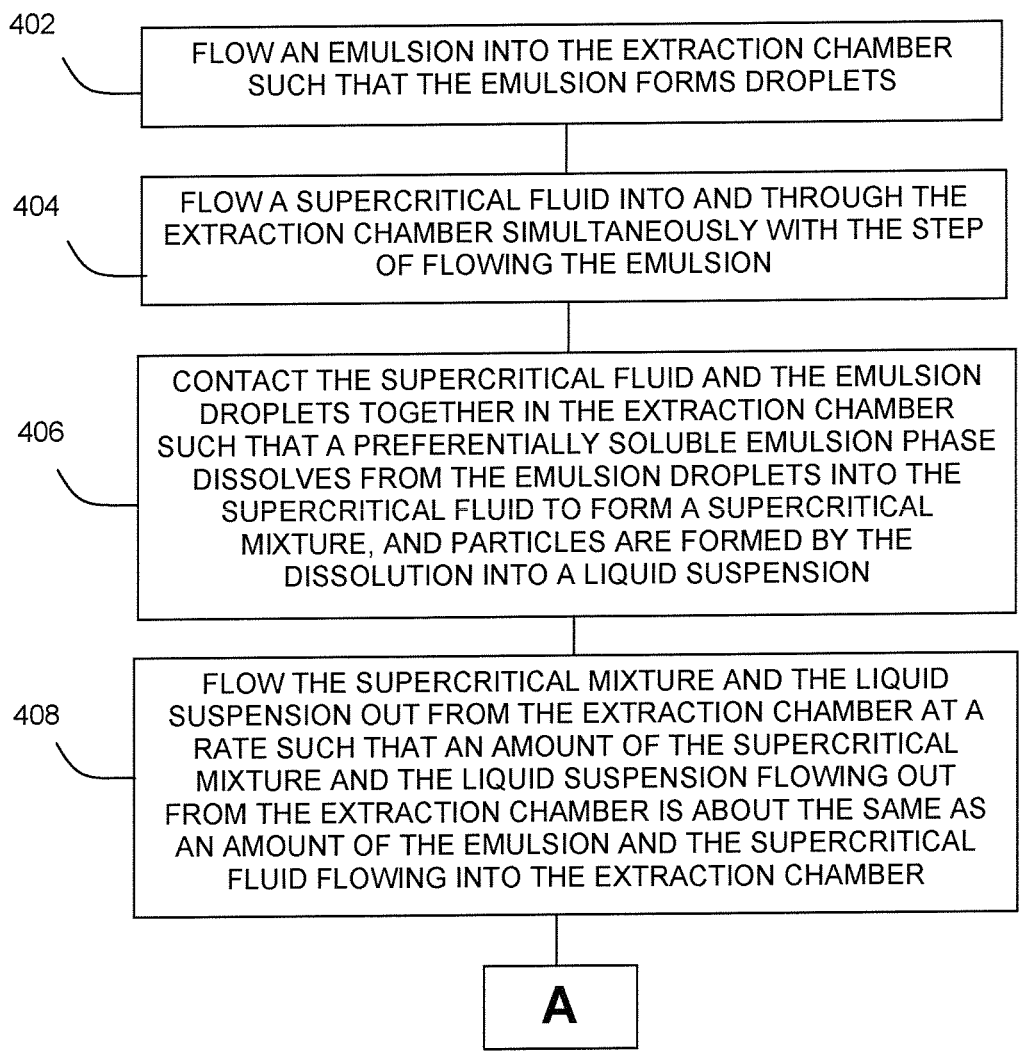
FIG. 4 is a block diagram of a method according to the invention.

With reference to FIGS. 1 and 4, the emulsion pump 126 supplies emulsion (step 402), and the supercritical fluid pump 124 supplies supercritical fluid (step 404), to the extractor 110. The supercritical fluid is dispersed upward into the extraction chamber 140 through the frit 142 at the first end 114 of the extractor 110.

Simultaneously, the emulsion is sprayed or pumped downward into the extractor 110 through the nozzle 144 at the upper second end 116. The supercritical fluid flows through the extraction chamber 140 by passing through the frit 142, the liquid phase 146, the packed bed 148, and the space 150 in the upward direction as indicated by the directional arrow labeled SUPERCRITICAL FLUID.

Preferably, the emulsion is sprayed or jetted into the space 150 and forms very small droplets 152 (step 402). As the emulsion jet is introduced into the extraction space 150, it is atomized into the small droplets 152 by a jet breakup caused by the passage through the openings in the nozzle 144. Mass transfer between the solvent contained in the emulsion droplets and supercritical fluid results in both supersaturation and precipitation of the solid within the droplets in the form of fine particles. The flow rates of both the emulsion and supercritical fluid are optimized and tuned in order to provide maximum removal of the solvent from the emulsion. The upper or maximum solid particles size is limited by the amount of solute or material dissolved within the droplets 152, that is, the concentration of the solute can affect particle size. The rate of solvent extraction provides control of the particle precipitation rate, and therefore influences both the number and solid-state properties (e.g. crystallinity and polymorphism) of produced particles. Composite particles can be obtained by co-precipitation of solutes or by material encapsulation a multiple emulsions system.

The droplets 152 are urged downward both by gravity and by the force of the emulsion, and flow in the direction indicated by the directional arrow labeled EMULSION. The emulsion droplets 152 travel or are carried through the packed bed 148 and into the liquid phase 146. Accordingly, the droplets 152 and the supercritical fluid form contra-current flows with the supercritical fluid flowing in a first direction and the droplets 152 flowing in an opposite second direction.

The supercritical fluid intermingles with and contacts the emulsion droplets 152 during the countercurrent current flows (step 406). The packed bed 148 increases the surface area, and thus the contact, between the emulsion and the supercritical fluid. The solvent in the emulsion droplet 152 is dissolved into the flow of supercritical fluid. The supercritical fluid thus removes the solvent from the emulsion droplet 152. The solvent removal results in the material of interest that was dissolved in the emulsion droplet 152 precipitating into the remaining phase, thus forming a particle suspension in the phase that is relatively less soluble in the supercritical fluid.

The particle suspension continues to flow downward toward, and into, the liquid phase 146. The liquid phase/suspension is purged from the extraction chamber 140 via the release valve 130. The aqueous suspended particles are recovered from the purged liquid phase.

The supercritical fluid bears the dissolved solvent upward to the backpressure regulator 132. The supercritical fluid and solvent exit the extraction chamber 140 via the backpressure regulator 132. Optionally, the supercritical fluid and solvent are recovered for reuse.

The apparatus 100 operates in a continuous manner with the aid of the backpressure regulator 132 and the release valve 130. The backpressure regulator 132 and the release valve 130 communicate with the pumps 124, 126, and cooperate with each other to maintain the balance of feed and exit flows of the supercritical fluid and the emulsion (step 508). The method shown in FIG. 4 can end at step 508, alternatively the process can continue as described hereinbelow.

Figure 2:
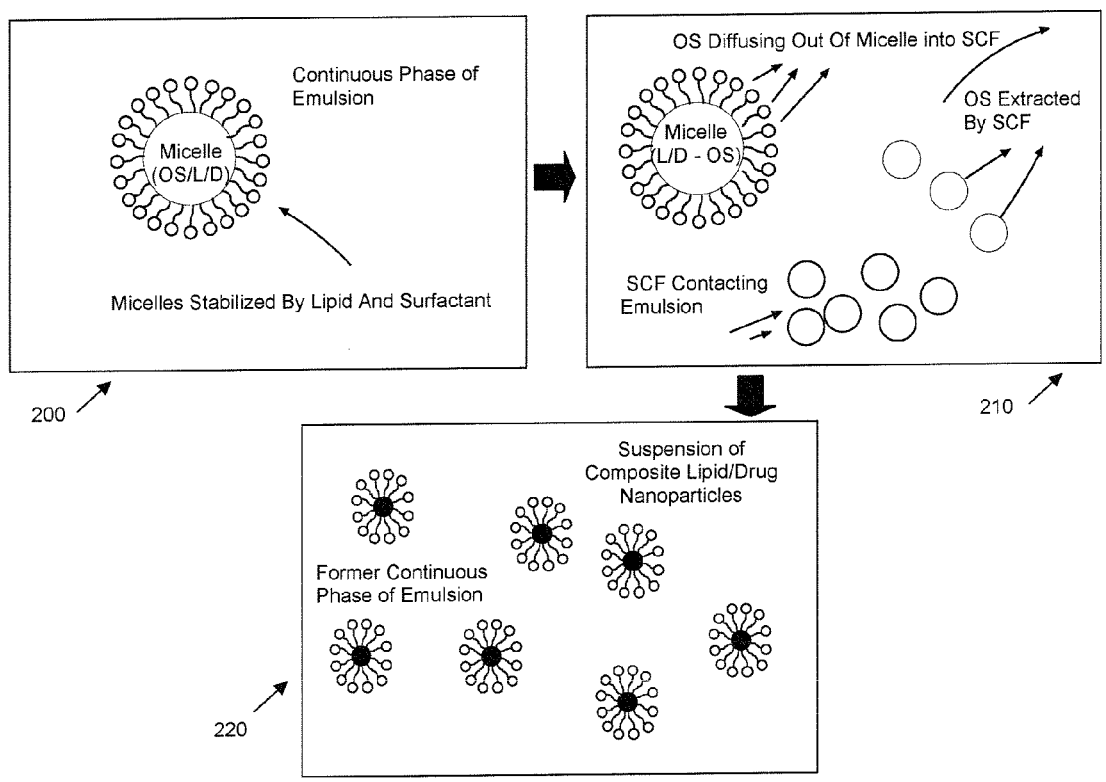
FIG. 2 is a schematic flow chart that illustrates the steps of the method.

FIG. 2 is a schematic representation showing various aspects of the method of the invention. Box 200 shows a representative emulsion micelle comprising an organic solvent (OS) having a lipid (L) and a drug (D) dissolved therein. The micelle depicted in Box 200 represents the discontinuous phase of the emulsion formed by emulsifying the organic solution containing the dissolved drug and lipid in a liquid. A co-surfactant may also be present in the micelle, and a surfactant may be present in the liquid that constitutes the continuous phase of the emulsion.

Box 210 shows the organic solvent diffusing out of the micelle and into the supercritical fluid (SCF), which is contacting the emulsion while the supercritical fluid is being maintained in a supercritical state. In Box 210, the supercritical fluid is shown in the form of bubbles, which can be formed by pumping the supercritical fluid through the frit.

Box 220 shows that as the organic solvent continues to be extracted from the micelles, the solvating power of the organic solvent remaining in the micelles diminishes, and the lipid and drug supersaturate the solution and precipitate as solid composite lipid/drug nanoparticles. The supercritical fluid bearing the organic solvent flows away from the solid lipid/drug composite nanoparticles, which are dispersed or suspended in the liquid. The dispersion or suspension of solid composite/lipid nanoparticles in the liquid can be removed from the pressure vessel, depressurized, and used to deliver drugs to an animal organism such as a human being. Alternatively, the suspension or dispersion of solid composite lipid/ drug nanoparticles can be further processed to obtain a paste or dry powders. The solid composite lipid/drug nanoparticles preferably consist essentially of one or more lipids and one or more drugs, but may also consist of small amounts of one or more surfactants and/or a co-surfactants and very small amounts (<~20 ppm) of one or more residual organic solvents.

Figure 3:
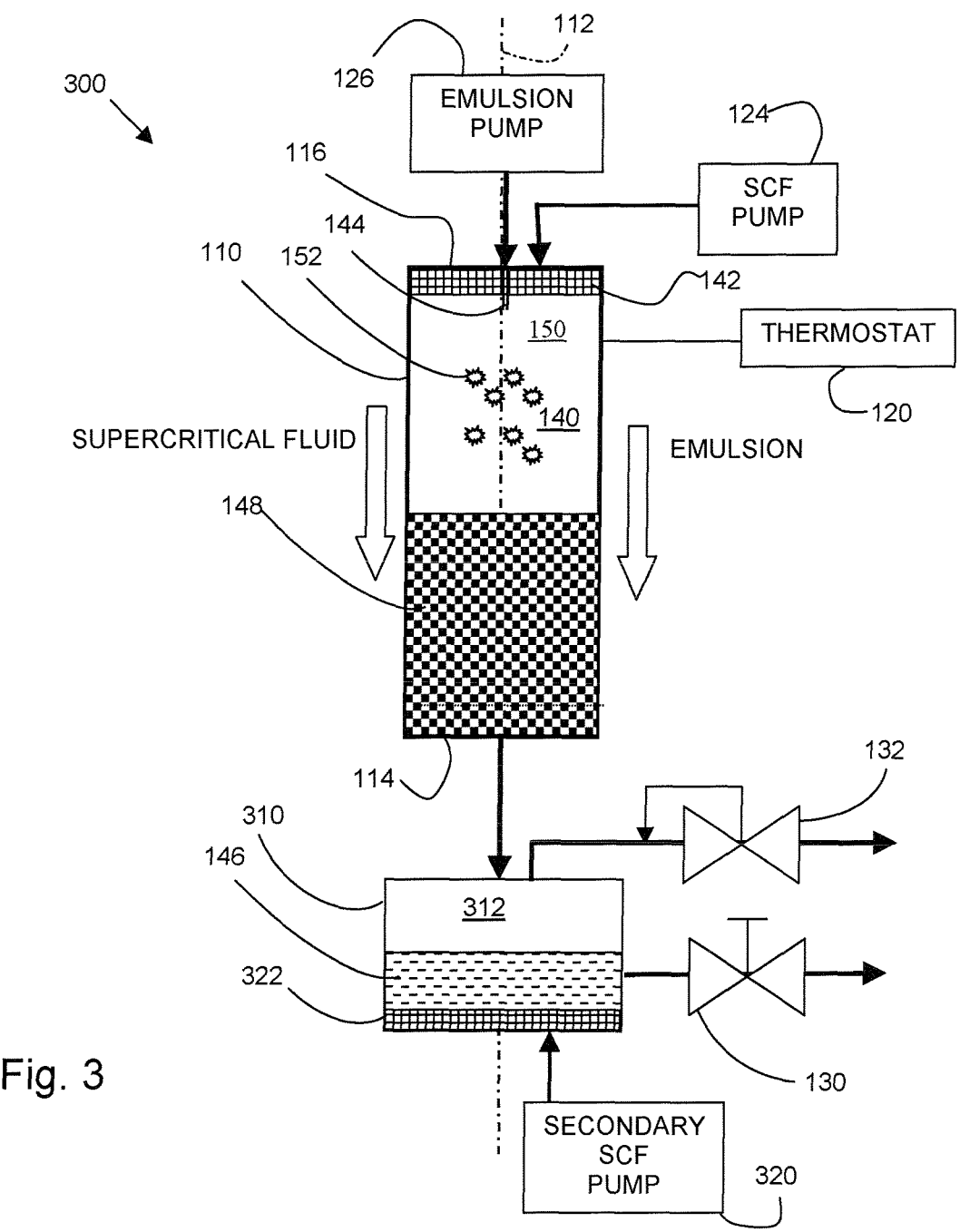
FIG. 3 is a schematic drawing of a second apparatus for use in accordance with another method of the invention.

A second embodiment of the invention comprising an apparatus 300 for use with another method according to the invention is shown in FIG. 3. The apparatus 300 has many parts that are substantially the same as corresponding parts of the apparatus 100; this is indicated by the use of the same reference numbers in FIGS. 1 and 3. Similar to the first embodiment, the apparatus 300 simultaneously disperses an emulsion and a supercritical fluid. However, the flows of the emulsion and the supercritical fluid are parallel or co-current in the second embodiment, rather than counter to each other.

Figure 5:
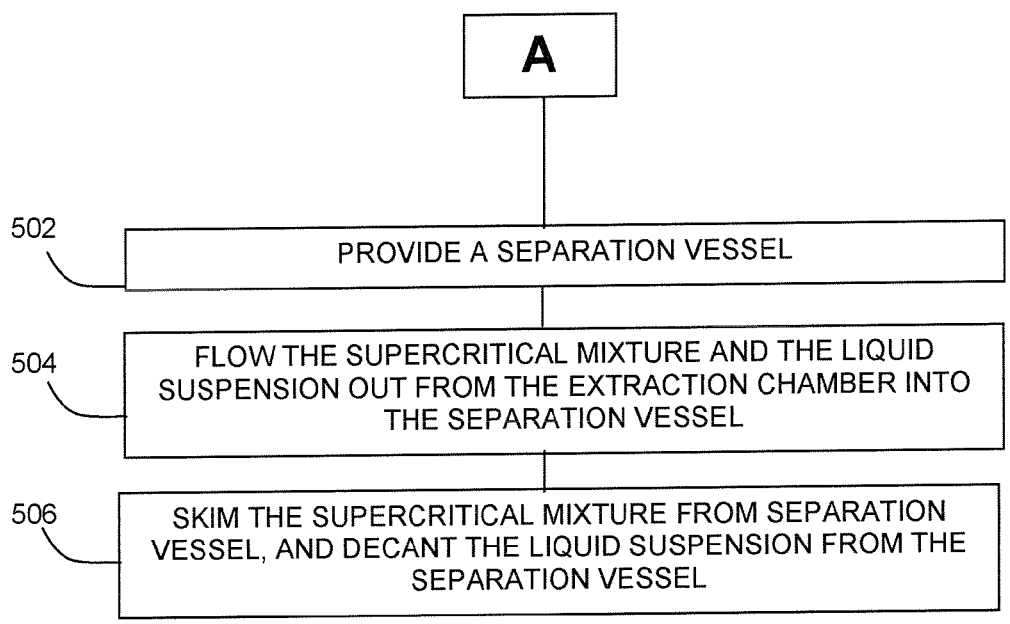
FIG. 5 is a block diagram of another method according to the invention.
Figure 6A:
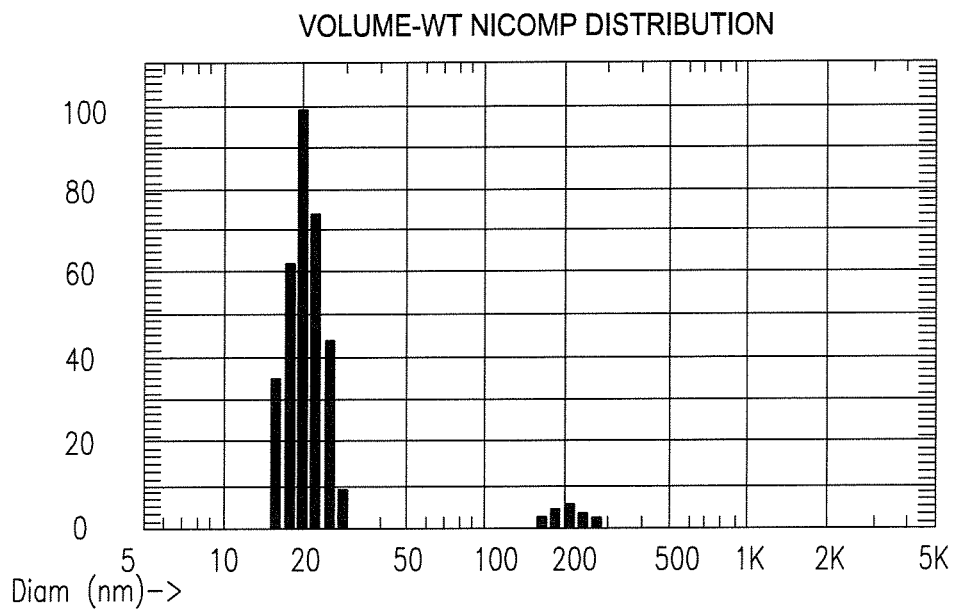
FIGS. 6(a) through 6(d) are graphs showing the particle size distribution of the solid composite lipid/drug nanoparticles produced in Example 1.
Figure 6B:
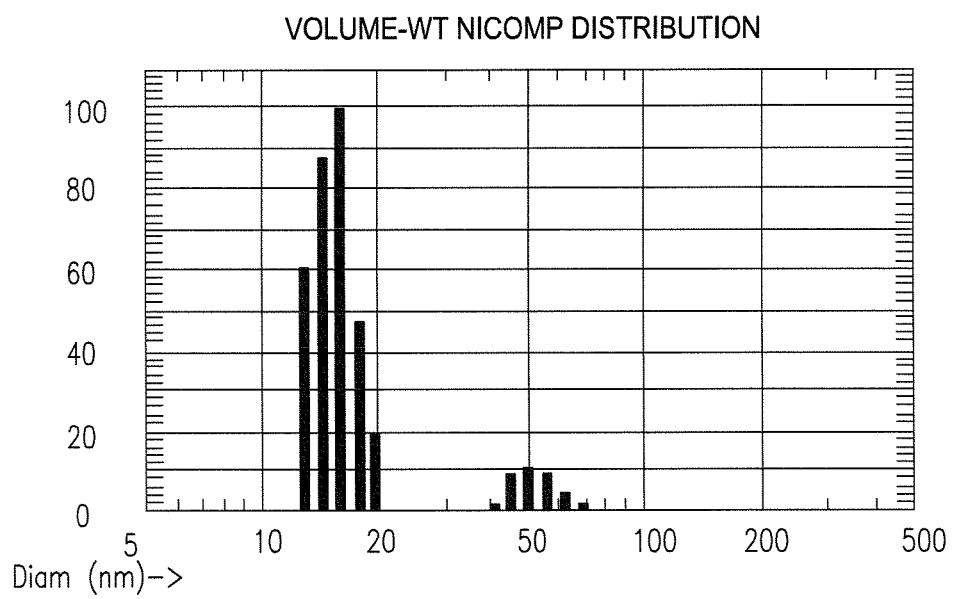
Figure 6C:
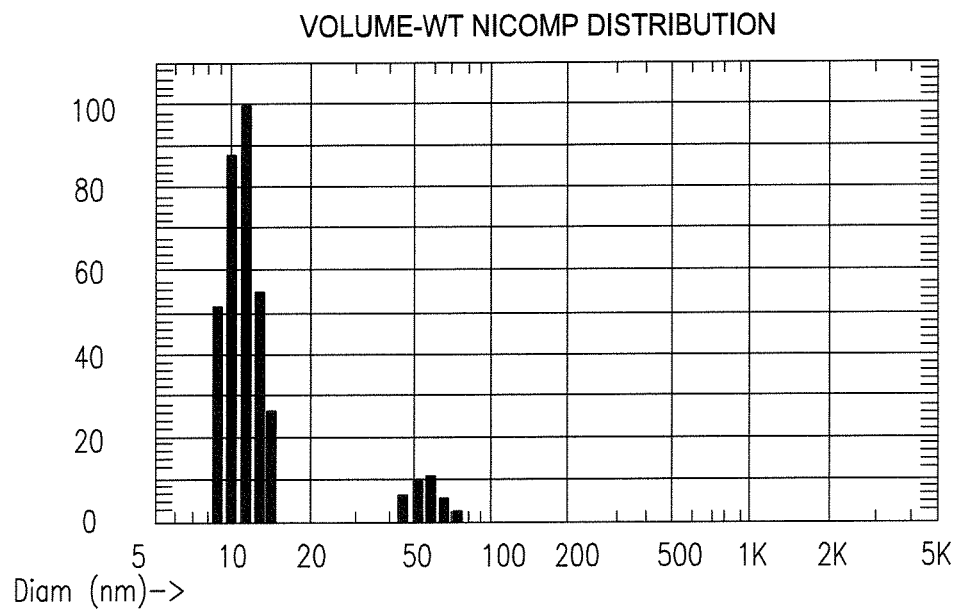
Figure 6D:
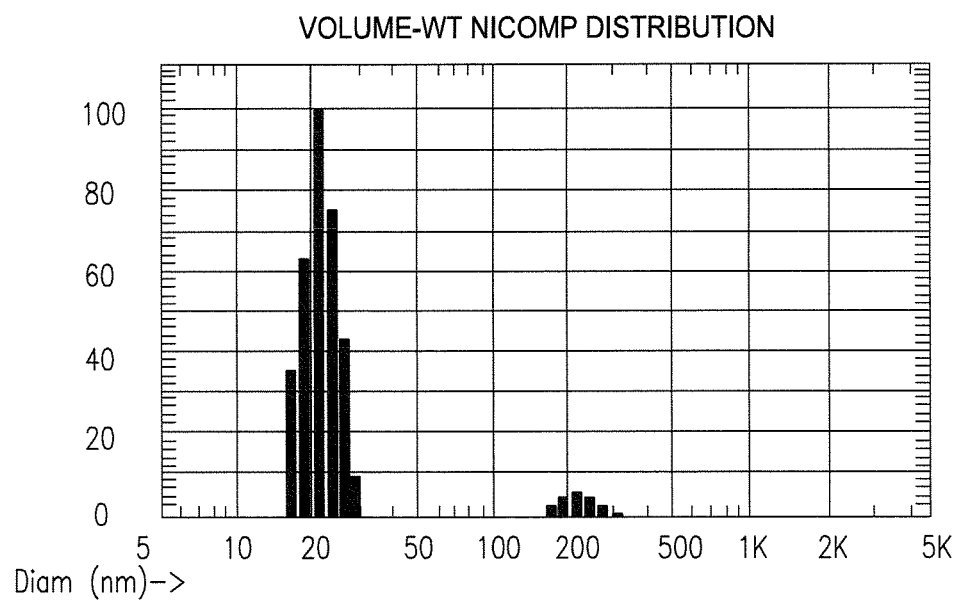

The apparatus 300 includes a separation vessel 310 (step 502 in FIG. 5). The separation vessel 310 has an inner surface defining a separation chamber 312. The separation vessel 310 preferably has cyclone or cylinder geometry. The supercritical fluid pump 124 communicates with the second end 116 of the extractor 110, rather than the first end 114, and the frit 142 overlays the second end 116 rather than the first end 114, as in the first embodiment.

A secondary supercritical fluid pump 320 supplies supercritical fluid to the vessel 310 through a secondary frit 322. The secondary frit 322 overlays a bottom portion of the inner surface of the vessel 310 inside the chamber 312.

The separation vessel 310 can also be used in conjunction with other embodiments of the invention. For example, the separation vessel 310 can be placed in fluid communication with the apparatus 100, and therefore used with a contra-current continuous flow apparatus. The addition of the separation vessel 310 to an extraction device according to the invention can increase the purity and/or reduce the residual solvent content of the resultant particles.

During operation of the apparatus 300, the thermostat 120 controls the temperature of the extractor 110 to a predetermined and equilibrated temperature. The supercritical fluid pump 124 supplies supercritical fluid to the extractor chamber 140 at the first end 116 of the extractor 110. The supercritical fluid flows through the frit 142 and downward into the chamber 140. Simultaneously, the emulsion pump 126 supplies emulsion to the extractor 110 through the nozzle 144. The emulsion flows through the nozzle 144 and downward into the chamber 140. The emulsion breaks into the droplets 152 as it exits the nozzle 144 through the nozzle openings. The droplets 152 and the supercritical fluid flow co-currently together downward through the chamber 140 and further through the packed bed 148. The co-current flow is a multi-phase flow.

The droplets 152 intimately contact the supercritical fluid during the co-current flow. Because of the contact, the solvent present in the emulsion is dissolved or extracted into the supercritical fluid. Material dissolved in the emulsion precipitates out in the form of small particles as a result of the solvent extraction.

With reference to FIGS. 3 and 5, the multi-phase flow and the particles produced by the extraction process are communicated to the separation vessel 310 (step 504). The steps illustrated in FIG. 5 end with step A and the steps illustrated in FIG. 5 begin with step A to indicate that the optional additional process steps shown in FIG. 5 may be performed subsequent to or concurrent with the steps shown in FIG. 4.

In the separation vessel 310, the aqueous suspension of particles and supercritical fluid mixture (supercritical fluid+ solvent) are separated (step 504). The liquid suspension is generally heavier than the supercritical fluid mixture. Thus, the separator 310 can decant the liquid suspension layer 146 and skim the supercritical fluid mixture layer (which occupies a substantial remaining portion of the chamber 312). Preferably, the separation vessel 310 has heaters (not shown) that communicate with the thermostat 120. The thermostat 120 controls the temperature in the separation vessel 310.

The secondary supercritical fluid pump 320 can supply supercritical fluid into the chamber 312 through the secondary frit 322. The secondary supercritical fluid pump 320 can both control the pressure in the chamber 312, and also provide a second flow of supercritical fluid through the liquid suspension layer 146 so as to remove residual solvent and further purify the precipitated particles.

The apparatus 300 operates in a continuous manner with the aid of the backpressure regulator 132 regulating the supercritical fluid flow, and the release valve 130 controlling the liquid suspension flow. The regulator 132 and release valve 130 together adjusting the exit flows with reference to inflows by the pumps 124, 126.

The apparatus and methods described in the present application can be used scaled up for continuous commercial-scale production of dispersions or suspensions of solid composite lipid/drug nanoparticles in water or other liquids, which can, if desired, be further processed to obtain dry powders or concentrated to form pastes. The method is particularly effective for the production of nanosuspensions with average particle sizes as small as 5 nm. By varying the concentration of the lipid, drug, organic solvent and the fluid, robust size control of the resulting solid composite lipid/drug nanoparticles can be obtained. The particles tend to be monodisperse, and can have drug loadings up to 50%. Particles having an average particle size of from about 5 nm to about 100 nm are particularly preferred.

The method and apparatus produce a high yield of solid composite lipid/drug nanoparticles, which can be recovered at relatively high concentration dispersed or suspended in the liquid. The solid composite lipid/drug nanoparticles exhibit very low residual solvent content (<20 ppm), and can be produced using non-toxic organic solvents. The process is a low shear, low temperature process, which prevents degradation of the drug during processing.

In a further embodiment of the method of the invention, the suspension of solid composite lipid/drug nanoparticles can be further be converted into a solid porous mass via lyophilization with a cryoprotectant. The solid porous mass can be easily redispersed in an aqueous media.

Solid composite lipid/drug nanocomposites according to the invention can increase the bioavailability of drugs in animal organisms. The lipid aids in the absorption or uptake of the drug into the animal tissue. The solid lipid/drug composite nanoparticles according to the invention are suitable for injections, topical/ophthalmic preparations and aerosols.

The following examples are intended only to illustrate the invention and should not be construed as imposing limitations upon the claims. Unless specified otherwise, all ingredients are commercially available from such common chemical suppliers as Sigma Aldrich, Inc. (St. Louis, Mo.) and/or Fisher Scientific International, Inc. (Hanover Park, Ill.).

EXAMPLE

Preparation of Emulsions

Four organic solutions (Examples 1-4, respectively) were prepared by dissolving 5 percent of a lipid (GLUCIRE 50/13) and the amounts shown in Table 1 of either Indomethacin or Ketoprofen in chloroform (all amounts are specified as weight percents relative to the weight of the organic solvent). The resulting organic solutions were then dispersed in an aqueous 0.13% w/w of sodium glycocholate solution in the amounts shown in Table 1 in parts by weight relative to water to form coarse oil-in-water (O/W) emulsions. The resulting emulsions were then homogenized using a homogenizer commercially available from Microfluidics, Inc. (Newton, Mass.) at 16,000 p.s.i. in 3 passes.

TABLE 1

| Example | Drug | Weight % of Drug in Solvent | Weight % of Organic Solution in Water |
| --- | --- | --- | --- |
| 1 | Indomethacin | 15 | 10 |
| 2 | Indomethacin | 10 | 30 |
| 3 | Indomethacin | 15 | 30 |
| 4 | Ketoprofen | 15 | 30 |

Precipitation of Nanoparticles

An apparatus such as shown in FIG. 1 was used to precipitate solid composite lipid/drug nanoparticles as a suspension in water. About, 100-200 milliliters (ml) of each emulsion was pumped using an emulsion pump into an extraction chamber at a constant flow rate. Simultaneously, a supercritical fluid pump was used to pump supercritical $CO_2$ into the extraction chamber through a frit. The extraction chamber was maintained at a constant pressure and temperature of 8 megapascal (MPa) and 318 Kelvin (K), respectively. The flow rates of the supercritical $CO_2$ and the emulsion through the extraction chamber were maintained constant: 50 g/min for $CO_2$; and 5 ml/min for the emulsions. Counter current extraction of the solvent from the emulsion droplets caused the solid composite lipid/drug nanoparticles to precipitate into an aqueous liquid. The solid composite lipid/drug nanoparticles were suspended in the aqueous liquid, and were stabilized by the surfactants present in the emulsion. The suspension was removed from the extraction chamber at a constant rate of 55 g/min through the release valve. The suspensions of solid composite lipid/drug nanoparticles were then analyzed.

Analysis of the Nanoparticles

Analysis of the aqueous colloidal suspensions of solid composite lipid/drug nanoparticles was performed using a DLS. FIGS. 6a through 6d are graphs illustrating the particle size distribution of the solid composite lipid/drug nanoparticles obtained from Examples 1 through 4, respectively. The analysis of the particles is numerically illustrated in Table 2 below:

TABLE 2

| Example | Vol. Avg. | Std. Dev. | No. Avg. | Std. Dev. |
| --- | --- | --- | --- | --- |
| 1 | 27 nm | 27 nm | 17 nm | 17 nm |
| 2 | 22 nm | 17 nm | 13 nm | 10 nm |
| 3 | 39 nm | 32 nm | 21 nm | 17 nm |
| 4 | 22 nm | 13 nm | 10 nm | 7 nm |

Additional advantages and modifications will readily occur to those skilled in the art. Therefore, the invention in its broader aspects is not limited to the specific details and illustrative examples shown and described herein. Accordingly, various modifications may be made without departing from the spirit or scope of the general inventive concept as defined by the appended claims and their equivalents.

What is claimed is:

1. A method for producing a suspension or dispersion of solid composite lipid/drug nanoparticles in an aqueous liquid comprising:

dissolving a lipid that is a solid phase material at 1 atmosphere pressure and 15° C. temperature and a drug in a suitable organic solvent to form a solution, wherein the weight ratio of the drug to the lipid in the solution is from about 5:95 to about 40:60 and wherein the drug/lipid loading in the solution is from 1% to about 50% by weight of the organic solvent;

emulsifying the solution in the aqueous liquid to form an emulsion having a discontinuous phase of micelles comprising the organic solvent, the drug and the lipid, and a continuous phase comprising the aqueous liquid; and contacting the emulsion with a supercritical fluid under conditions suitable to keep the supercritical fluid in a supercritical state, whereby the supercritical fluid extracts the organic solvent from the micelles, causing the lipid and the drug to precipitate from the micelles into the aqueous liquid in the form of solid composite lipid/drug nanoparticles that are suspended or dispersed in the aqueous liquid.

2. The method according to claim 1 wherein a surfactant is dissolved in the aqueous liquid before the solution is emulsified in the aqueous liquid.

3. The method according to claim 2 wherein a co-surfactant is dissolved in the solution before the solution is emulsified in the aqueous liquid.

4. The method according to claim 1 wherein the supercritical fluid is supercritical carbon dioxide.

5. The method according to claim 4 wherein the organic solvent is chloroform.

6. The method according to claim 1 wherein the average particle size of the solid composite lipid/drug nanoparticles is from about 5 nm to about 1000 nm.

7. The method according to claim 1 wherein the emulsion and the supercritical fluid contact each other as contra-current flows in an extraction chamber.

* * * * *